United States Patent [19]

Winterton et al.

[11] Patent Number: 5,523,012

[45] Date of Patent: * Jun. 4, 1996

[54] HYDROGEN PEROXIDE DISINFECTION SOLUTIONS

[75] Inventors: Lynn C. Winterton, Roswell; Kai C. Su, Alpharetta, both of Ga.

[73] Assignee: Ciba-Geigy Corporation, Ardsley, N.Y.

[ * ] Notice: The portion of the term of this patent subsequent to May 11, 2010, has been disclaimed.

[21] Appl. No.: 733,115

[22] Filed: Jul. 19, 1991

[51] Int. Cl.$^6$ .................................................. A61L 2/18
[52] U.S. Cl. ............................ 252/106; 134/42; 422/30
[58] Field of Search ........................ 252/95, 98, 106; 134/27, 42; 422/30

[56] References Cited

U.S. PATENT DOCUMENTS

| | | | |
|---|---|---|---|
| 3,882,036 | 5/1975 | Krezanoski et al. | 252/106 |
| 3,912,451 | 10/1975 | Gaglia, Jr. | 21/58 |
| 4,046,706 | 9/1977 | Krezanoski et al. | 252/106 |
| 4,323,467 | 4/1982 | Fu | 252/106 |
| 4,414,127 | 11/1983 | Fu | 252/95 |
| 4,500,441 | 2/1985 | Tanaka et al. | 252/89.1 |
| 4,585,488 | 4/1986 | Giefer | 134/27 |
| 4,743,447 | 5/1988 | Le Rouzic et al. | 424/130 |
| 4,767,559 | 8/1988 | Kruse et al. | 252/106 |
| 4,775,424 | 10/1988 | Wisotzki et al. | 134/42 |
| 4,812,173 | 3/1989 | Tsao et al. | 134/27 |
| 4,820,352 | 4/1989 | Riedhammer et al. | 134/30 |
| 4,880,601 | 11/1989 | Andermann et al. | 422/28 |
| 4,889,689 | 12/1989 | Tsao | 422/30 |
| 5,017,238 | 5/1991 | Chromecek et al. | 134/7 |
| 5,145,644 | 9/1992 | Park et al. | 422/28 |

FOREIGN PATENT DOCUMENTS

| | | |
|---|---|---|
| 0441389 | 8/1991 | European Pat. Off. . |
| 3626082 | 2/1988 | Germany . |
| WO86/05695 | 10/1986 | WIPO . |

*Primary Examiner*—Gary P. Straub
*Assistant Examiner*—Timothy C. Vanoy
*Attorney, Agent, or Firm*—Wenderoth, Lind & Ponack

[57] ABSTRACT

The efficacy of buffered $H_2O_2$ disinfecting formulations for contact lenses is improved by incorporationg into such formulations a surface active agent.

7 Claims, 1 Drawing Sheet

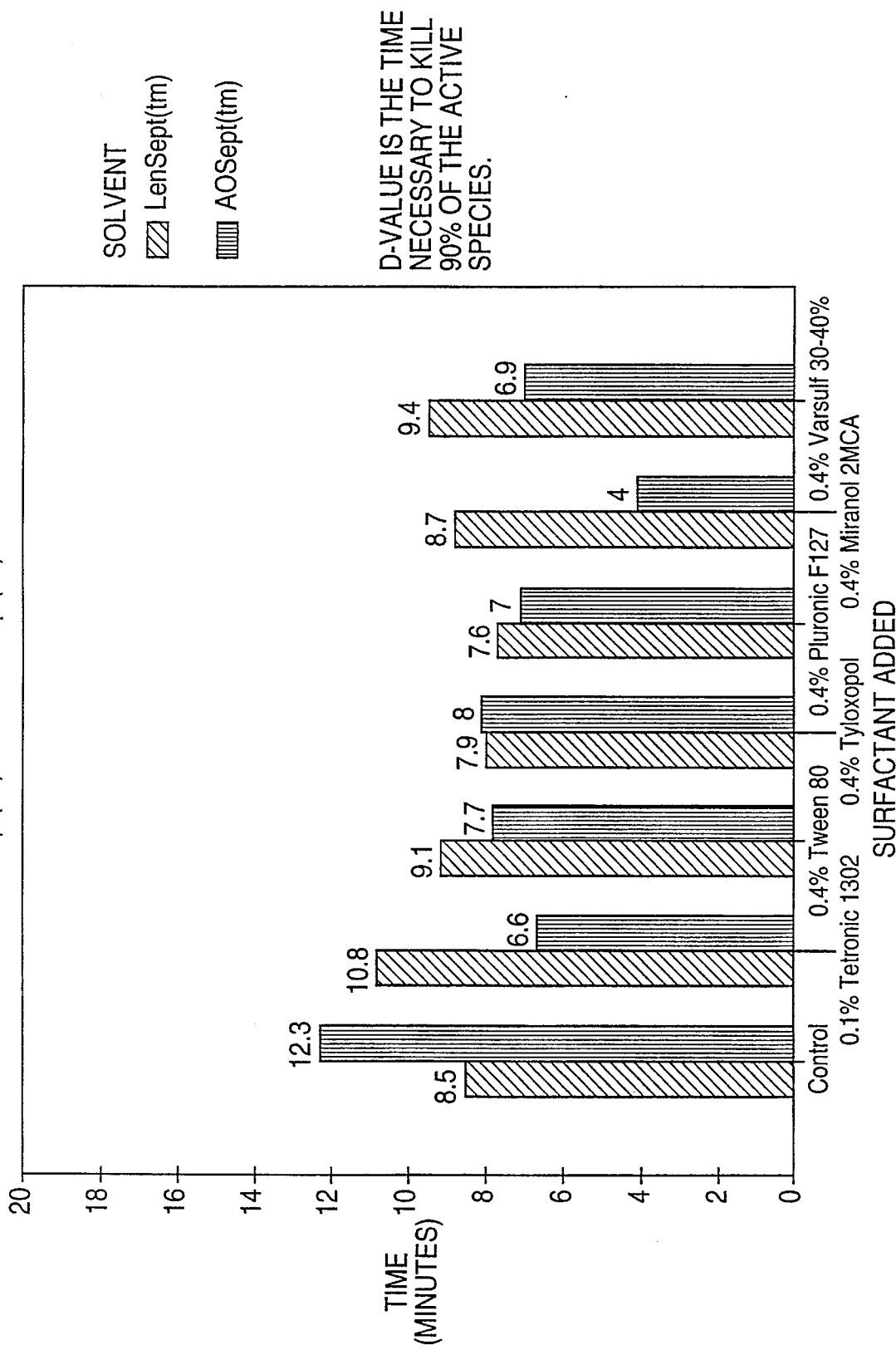

HYDROGEN PEROXIDE DISINFECTION SOLUTIONS

The present invention provides an improvement in hydrogen peroxide disinfection solutions. Specifically, the invention provides improvement in such disinfection solutions employed in the disinfection of contact lenses.

BACKGROUND OF THE INVENTION

Disinfecting solutions for use with contact lenses are well known in the art and the use of such lenses involves a daily disinfecting treatment. Flexible, or soft, contact lenses are generally made from hydrophilic polymers and the hydroxy groups of these lenses attract and retain substantial amounts of water in the plastic which results in difficulties during cleaning and sterilization.

Furthermore, hydrophilic flexible contact lenses have a tendency to complex with and concentrate certain preservatives and disinfecting agents used in sterilizing conventional contact lenses. If these preservatives come into contact with the cornea they can cause severe irritation and burning.

Hydrogen peroxide systems, and particular a 3% hydrogen peroxide solution, have emerged as the disinfectant of choice for all types of daily and extended wear hydrogen lenses. The primary reason for its increasing popularity is its rapid kill of microbial contaminants and its non-residual character. After hydrogen peroxide disinfects lenses, it can be converted into innocuous by-products which are compatible with ocular physiology. See Krezanoski et al., "Journal of the American Optometric Association", Vol. 59, Number 3, pages 193–197 (1988).

A great deal of patent literature is available concerning hydrogen peroxide contact lens disinfection systems. Reference is made in this respect to the following:

Gaglia, Jr., U.S. Pat. No. 3,912,451
LeRouzic et al., U.S. Pat. No. 4,743,447
Davies et al., International Pat. Publication WO 86/05695
Andermann et al., U.S. Pat. No. 4,880,601
Giefer, U.S. Pat. No. 4,585,488

In general, the hydrogen peroxide systems involve a hydrogen peroxide-containing disinfecting solution into which the contact lenses to be disinfected are placed and allowed to remain for a required period of time. Nascent oxygen is released providing a germicidal effect. Following the requisite time period a purposeful inactivation of the hydrogen peroxide is conducted, for example, with a platinum catalyst. Following inactivation, the contact lens may be reinserted into the eye.

The hydrogen peroxide disinfecting solutions may be of the buffered or unbuffered type. As examples, AOSept ® is a stabilized 3% hydrogen peroxide solution made isotonic with sodium chloride and buffered to an approximate pH 6.9 with phosphates. On the other hand, LenSept ® is a non-buffered 3% hydrogen peroxide formulation.

BRIEF DESCRIPTION OF THE DRAWING

The FIGURE of the drawing shows the results of tests comparing the killing efficacy of various surfactants in buffered and unbuffered hydrogen peroxide solutions.

DESCRIPTION OF THE INVENTION

The present invention is based upon the discovery that it is possible to improve the killing effectiveness and the rate of kill of both fungi and bacteria by modifying the buffered hydrogen peroxide disinfecting solution to incorporate therein an ocularly compatible surface active agent in a specified amount. Thus, the invention provides an improvement in a buffered hydrogen peroxide disinfecting solution which comprises incorporating into said solution from about 0.1% to about 1.0% by weight of the solution of an ocularly compatible surface active agent.

Gaglia, Jr., U.S. Pat. No. 3,912,451 discloses the buffered hydrogen peroxide solutions of the type to which the present invention can be applied and for which improvement can be achieved.

By addition of the surface active agent to the buffered hydrogen peroxide disinfecting solution it is possible to improve the killing effectiveness and the rate of kill of both fungi and bacteria.

With most 3% hydrogen peroxide formulations, there are some viable organisms remaining even after a 30 minute soaking time of the contact lens. However, with the improvement of this invention, it is possible to provide a formulation in which there are no viable organisms after a 30 minute soaking time. With the current peroxide formulations there is a "lag" time between the time when the organisms are placed in the peroxide and the time when actual killing occurs. With the addition of the surface active agent, this "lag" time is reduced significantly and the rate of kill is enhanced.

In the literature it has been indicated that hydrogen peroxide formulations are not effective for contact lenses without a full-strength soaking for a minimum of 55 minutes. With this invention, however, it is possible to reduce considerably the disinfection time and obtain more complete disinfection.

The hydrogen peroxide formulations to which the surface active agent is added are of the buffered type. In general, in formulating such solutions a 3% by weight hydrogen peroxide solution is formulated to contain 0.85% by weight sodium chloride. Upon the ultimate conversion of the $H_2O_2$ to water and oxygen by catalyst this will yield an approximately isotonic saline solution as the final product. With the sodium chloride there is added to the $H_2O_2$ solution the necessary buffer system to buffer the 0.85% aqueous sodium chloride solution to the desired pH of about 6.9 to 7.1.

The buffer system may comprise a suitable combination of monobasic sodium phosphate and dibasic sodium phosphate. Other satisfactory buffer systems may be employed which give substantially equivalent results in buffering to a pH of 6.9 to 7.1. As examples there can be mentioned tartrate, succinate and glycine buffers or the MacIlvaine phosphate-citrate buffer as described in *J. Biol. Chem.*, 183 (1921).

To the solution can also be added a hydrogen peroxide stabilizer such as sodium stannate or sodium nitrate. Such stabilizers are known in the art. In addition, as the stabilizer there can be employed diethylene triamine penta (methylenephosphonic acid) or a physiologically compatible salt thereof. See U.S. Pat. No. 4,889,689.

As an example of the buffered type hydrogen peroxide formulation, there can be mentioned the commercially available Aosept ® formulation.

In the broadest sense the surface active agents which can be used are those which are ocularly compatible and which function in the buffered hydrogen peroxide formulations to improve the killing effectiveness of such formulations. As specific examples of the materials the following may be mentioned.

Polyethylene-polyoxypropylene substituted ethylenediamine nonionic surfactants which are more commonly known as "Tetronic ®" type surfactants. These are also generally known by the generic name "poloxamine" and are commercially available from BASF-Wyandotte Corp.

Polyoxyethylene-polyoxypropylene nonionic surfactants sold under the trademark "Pluronic ®" by BASF-Wyandotte Corp. These surfactants are generally known as "poloxomers" and typically have a molecular weight of between about 2,000 and about 5,000.

Polysorbates, such as "Tween ®" surfactants (ICI Americas) including, for example polysorbate 20, 40, 60, 65, 80 and 85.

Tyloxapol, such as "Superinone ®" detergent (Winthrop). Miranol ® amphoteric surfactants from Miranol Inc. such as "Miranol ®" 2MCA which is lauryl sulfate salt of an amphoteric surfactant derived from coconut imidazoline. Varonic ® surfactants such as Varonic ® LI-63 and LI-67 which are ethoxylated glyceryl monococoates. These are commercially available from Sherex Chemical Company, Inc.

Varsulf anionic sulfosuccinates such as Varsulf SBFA-30 and Varsulf SBL-203. These are commercially available from Sherex Chemical Company, Inc.

The foregoing are merely illustrative and not exhaustive of the surface active agents which can be employed in the invention.

One skilled in the art will be able to readily determine whether a given surface active agent or mixture of such agents can be employed. First, it is necessary to determine that such agent or mixture of agents is ocularly compatible. Tests for determining such compatibility are well known in the art. Such agent or mixture must not cause irritation or damage to the eye of a contact lens wearer. Secondly, the agent or mixture must be one which improves the killing efficacy of the buffered $H_2O_2$ formulation. Standard challenge organisms are known against which the buffered $H_2O_2$ formulation alone and that formulation containing the surface active agent or mixture can be compared. It is not, of course, essential that the agent or mixture of agents improve the efficacy against every challenge organism, it being most important that the overall spectrum of activity be improved.

It is also to be noted that these surface active agents can be employed alone or in combination.

The surface active agent is added to the hydrogen peroxide formulation in an amount from about 0.1% to about 1.0% by weight of the formulation.

Particularly suitable for use in the invention are the nonionic poloxamine and poloxamer type surfactants disclosed in co-pending U.S. patent application Ser. No. 07/470,105 filed Jan. 25, 1990. These materials offer the further advantage of providing conditioning properties for the contact lenses by rendering the contact lens surface more wettable so that proteins, lipids and other tear film substituents do not adhere to and form deposits on the lens surface.

Also particularly suitable for use is a mixture of poloxamine 1302 (Tetronic ®) and polysorbate 80 (Tween ® 80) in amounts of 0.1% by weight and 0.4% by weight respectively.

EXEMPLIFICATION OF THE INVENTION

In order to exemplify the invention, compositions were compared for their relative disinfection capacity in respect to certain challenge microorganisms. The organisms tested are the FDA challenge organisms for disinfection solutions. The time required to kill 50% of the colony forming units (CFU) in solution was designated as the D-value. The initial solution employed was a commercially available AOSept ® solution which is a 3% buffered hydrogen peroxide solution also containing a hydrogen peroxide stabilizer. The solution of the present invention for comparison is prepared by adding to the commercially available AOSept ® initial solution, a mixture of polyoxamine 1302 (Tetronic ®) and polysorbate 80 (Tween ®80) in amounts sufficient to constitute 0.1% and 0.4% by weight respectively of the formulation. The results are shown in the table below:

| | D-VALUE (MINUTES) | |
|---|---|---|
| Organism | AOSept ® | Composition of the Invention |
| Pseudomonas aeruginosa | 0.54 | 0.53 |
| Staphylococcus epidermidis | 3.4 | 1.7 |
| Serratia marcescens | 2.4 | 3.5 |
| Candida albicans | 10 | 5.7 |
| Aspergillus fumigatus | 12.3 | 7.1 |

From the results it can be seen that the modified AOSept ® formulation of the invention is particularly effective against fungal spores and staphlococcal strains.

Further tests of the inventors have revealed that the improvement of the invention is applicable to only buffered hydrogen peroxide formulation and not to unbuffered solutions.

For purposes of this test *Aspergillus fumigatus* was chosen as the test organism. Two representative hydrogen peroxide formulations were used. AOSept ® as previously indicated, is the commercially available 3% stabilized hydrogen peroxide formulation that is buffered. LenSept ® is a commercially available stabilized hydrogen peroxide formulation which is not buffered. These solutions were compared for their killing efficacy as the controls. To each of these control formulations were added specified amounts of various surfactants and the killing efficacy of the resultant solutions was determined. The results are shown in the attached FIGURE of drawing. In these tests the D-value is the time necessary to kill 90% of the active species.

From the FIGURE it can be seen that in the case of the addition of the surfactants to the AOSept ® formulation, the killing efficacy was significantly increased in each case compared with the efficacy of the AOSept ® alone. However, with the unbuffered LenSept ® formulation, the addition of the surfactants either had an adverse affect on the killing efficacy (the time increased) or (in two cases) had a slight affect in improving it.

Having thus described the invention, what is claimed is:

1. In a buffered hydrogen peroxide formulation for disinfecting contact lenses, the improvement wherein said formulation contains from about 0.1% to about 1.0% by weight of the formulation of at least one ocularly compatible surface active agent which improves the killing efficacy of said buffered hydrogen peroxide formulation.

2. A formulation according to claim 1 wherein the surface active agent is a nonionic surface active agent.

3. A formulation according to claim 2 wherein the surface active agent is a poloxamine.

4. A formulation according to claim 1 wherein a mixture of two surface active agents is employed.

5. A formulation according to claim 4 which employs a mixture of a poloxamine type and a poloxamer type surface active agent.

6. A formulation according to claim 4 which employs a mixture of about 0.1% by weight of the formulation of a polyoxamine and about 0.4% by weight of the formulation of a polysorbate.

7. A method for improving the efficacy of a buffered hydrogen peroxide formulation for disinfecting contact lenses which comprises incorporating into said formulation from about 0.1% to about 1.0% by weight of the formulation of at least one ocularly compatible surface active agent which improves the killing efficacy of said buffered hydrogen peroxide formulation.

* * * * *